United States Patent
Ambekar et al.

(10) Patent No.: US 7,438,216 B2
(45) Date of Patent: Oct. 21, 2008

(54) MEDICAL INFORMATION ACCESS AND PROCESSING SYSTEM

(75) Inventors: Venu Ambekar, Coatesville, PA (US); Michal Cohen, Ramat-Hasharon (IL); John R. Zaleski, West Brandywine, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 266 days.

(21) Appl. No.: 11/382,546

(22) Filed: May 10, 2006

(65) Prior Publication Data

US 2006/0259326 A1 Nov. 16, 2006

Related U.S. Application Data

(60) Provisional application No. 60/679,419, filed on May 10, 2005.

(51) Int. Cl.
G06F 17/00 (2006.01)

(52) U.S. Cl. .................. 235/375; 235/380

(58) Field of Classification Search .......... 235/375, 235/380, 382, 382.5, 472.02; 705/2, 3, 9; 340/573.4, 539
See application file for complete search history.

(56) References Cited

U.S. PATENT DOCUMENTS

| | | | |
|---|---|---|---|
| 5,465,082 A | 11/1995 | Chaco | |
| 5,995,965 A | 11/1999 | Experton | |
| 6,342,839 B1 | 1/2002 | Curkendall et al. | |
| 6,464,136 B2 | 10/2002 | Walsh | |
| 6,785,674 B2* | 8/2004 | Vu | 707/3 |
| 2002/0013518 A1* | 1/2002 | West et al. | 600/300 |
| 2002/0038392 A1 | 3/2002 | De La Huerga | |
| 2003/0149598 A1* | 8/2003 | Santoso et al. | 705/2 |
| 2003/0210149 A1* | 11/2003 | Reisman et al. | 340/573.4 |
| 2004/0129716 A1* | 7/2004 | Naufel et al. | 221/9 |
| 2005/0055242 A1 | 3/2005 | Bello et al. | |
| 2006/0155584 A1* | 7/2006 | Aggarwal | 705/3 |
| 2006/0213981 A1* | 9/2006 | Suzuki et al. | 235/380 |
| 2007/0123956 A1* | 5/2007 | Sieracki et al. | 607/60 |
| 2007/0129983 A1* | 6/2007 | Scherpbier et al. | 705/8 |
| 2007/0150608 A1* | 6/2007 | Randall et al. | 709/228 |
| 2007/0222599 A1* | 9/2007 | Coveley et al. | 340/572.4 |

* cited by examiner

Primary Examiner—Thien M Le
(74) Attorney, Agent, or Firm—Alexander Burke (57) ABSTRACT

A medical information access and processing system includes a plurality of different wireless tag reader devices and a plurality of interfaces for receiving tag information, derived from reading a plurality of corresponding identification tags, from the tag reader devices. At least one repository of map information associates tag information received from the reader devices with reader device specific actions to be performed by a medical information access and processing system. A data processor uses the map information to associate tag information received from a specific reader device via an interface with a corresponding action to be performed by the medical information access and processing system and automatically initiates performance of the corresponding action by the medical information access and processing system.

20 Claims, 4 Drawing Sheets

Fig. 5

MEDICAL INFORMATION ACCESS AND PROCESSING SYSTEM

This is a non-provisional application based on provisional application Ser. No. 60/679,419 by Venu Ambekar, filed May 10, 2005.

FIELD OF THE INVENTION

The present invention relates to a processing system for accessing medical information, and in particular to a medical information access and processing system for using wireless means for entering information into such a system.

BACKGROUND OF THE INVENTION

In existing medical information access and processing systems, to perform tasks such as: patient registration, recall of patient-specific information, posting available lab results to patient record, etc., a user navigates, e.g. by entering data into the necessary fields via an input device, such as a keyboard, mouse, etc., to a specific screen and/or form in the user interface from where the user could perform the desired tasks. The navigation to a patient record may begin with a screen displaying a list of patients. The user may select the desired patient by browsing the entire list of patients or by searching a subset of patient records obtained through an alpha-search based upon: the patient identification number, medical record number (MRN) and/or patient name. Once the user finds the patient record screen, the user may perform tasks such as: updating profile and/or admission/discharge/transfer (ADT) information, etc. for that patient by using e.g. a keyboard and/or a mouse. In such medical information access and processing systems there are numerous screens and the user may need to navigate through multiple screens before arriving at the desired screen to perform a clinical workflow task. This becomes cumbersome for repetitious tasks and, due to the required manual entry of data at those screens, is subject to human errors that may result in potential hazards.

One approach to minimize these hazards is to associate workflow contexts required in clinical workflows with unique identifiers. These identifiers include patient MRN to launch patient record screen, national drug code (NDC) code to launch medication literature screen, etc. This identifying data, is stored in a medium such as a smartcard or an RFID tag or encoded in a UPC symbol via barcode labels. This information may be used to expedite the clinical workflow process. For example, to view a patient record, the clinical user locates an RFID tag or barcode label, containing patient identifying information, e.g. the patient wrist bracelet. The clinical user may use an RFID or barcode reader near the patient to read that information and supply that information directly to the medical information access and processing system. The medical information access and processing system, in response, displays the corresponding patient clinical record on a display device. This eliminates manually entering the patient information, thus maximizing the probability of retrieving the correct medical information.

Figure 1:
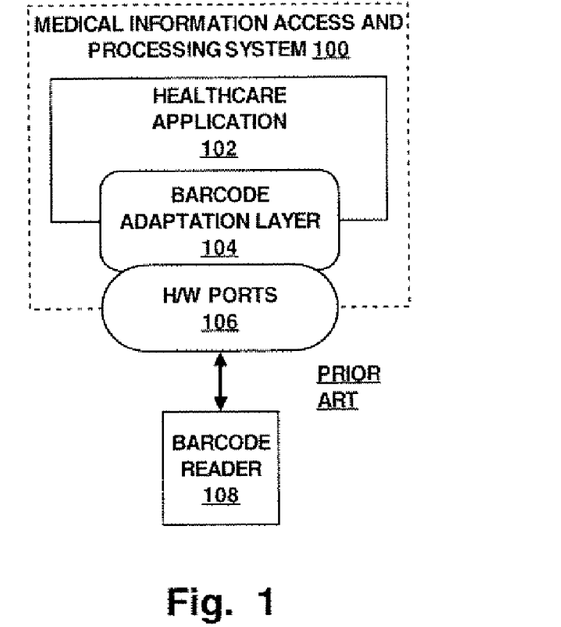
FIG. 1 and FIG. 2 are block diagrams illustrating prior art medical information access and processing systems.

A prior system using this approach is illustrated in FIG. 1. FIG. 1 illustrates a pertinent portion of a medical information access and processing system 100. A barcode reader 108 is coupled to a hardware port 106 in the medical information access and processing system 100. The hardware port 106 interoperates with an adaptation layer, identified in FIG. 1 as a barcode adaptation layer 104. The barcode adaptation layer 104 interoperates with the healthcare executable application 102. In operation, a barcode is fabricated to contain data representing a workflow context, such as a patient identifier. The barcode reader 108 is able to read the data contained in the barcode, e.g. by being passed over the barcode, or having the barcode brought within view of the barcode reader 108. The hardware port 106 receives the scanned data from the barcode reader 108. This data is supplied to the barcode adaptation layer 104 which controls the operation of the barcode reader 108 through the hardware port 106, and provides the scanned data to the healthcare executable application 102.

The adaptation layer (e.g. the barcode adaptation layer 104) is an executable procedure for controlling a reader of a specific technology (e.g. the barcode reader 108). That is, the barcode adaptation layer 104 is programmed to interface a specific executable application (e.g. healthcare executable application 102) to a specific hardware communications port 106 (e.g. COM port) and a specific barcode reader hardware device 108 (e.g. from a specific vendor). The adaptation layer 104, thus, is the enhancement of the healthcare executable application 102 that provides functionality to integrate clinical workflows with barcode reader 108 device functions. Consequently, the barcode adaptation layer 104 is tightly coupled with the healthcare executable application 102 and the medical information access and processing system 100 hardware and the local hardware port 106 (i.e. COM port) to which the barcode reader 108 is directly attached. The overall flow of data from the bar code reader 108 is implemented as event data generated by the hardware port 106 and supplied to the barcode adaptation 104 upon reading a valid barcode sequence (typically initiated by depressing a trigger on the bar code reader 108). The adaptation layer 104 maps these events to appropriate executable procedures, performing corresponding functions in the clinical workflow process implemented by the healthcare executable application 102.

Such systems are typically restricted to a single healthcare executable application, a specific information reading technology and a reader appliance of a specific brand or from a vendor. Supplementing an existing healthcare executable application with additional appliances of a different technology requires custom modification to the healthcare executable application, i.e. the addition of an adaptation layer, and the addition of extra hardware and/or software modules. This is an onerous, expensive and long term project. Similarly, adding reading devices of same technology but from a different vendor involves an effort analogous to adding new technologies. In systems with multiple executable applications it is even more challenging to use multiple input devices to invoke different workflow tasks in different executable applications, because the respective executable applications require the same modifications.

Figure 2:
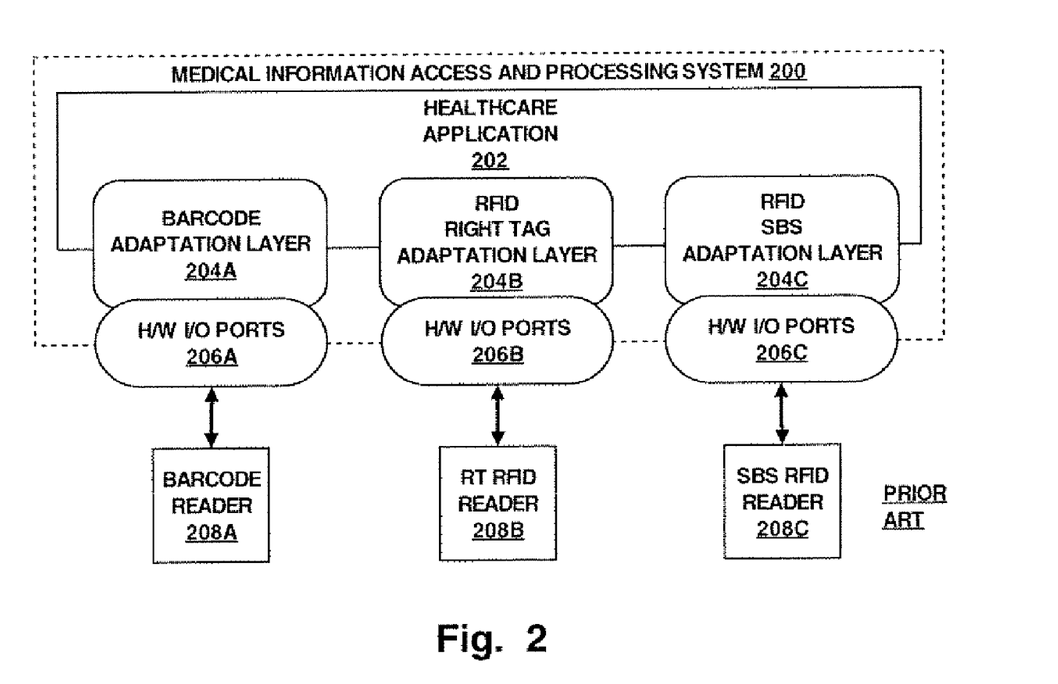

In FIG. 2, a medical information access and processing system 200 includes multiple information readers having different reading technologies and/or from different vendors. A barcode reader 208a, a right tag (RT) RFID reader 208b and an RFID reader 208c manufactured by Siemens Business Systems (SBS) are coupled to the medical information access and processing system 200. The barcode reader 208a is coupled to a hardware input/output (I/O) port 206a, the RF RFID reader 208b is coupled to a hardware I/O port 206b and the SBS RFID reader 208c is coupled to a hardware I/O port 206c. The hardware I/O port 206a interoperates with an adaptation layer identified as barcode adaptation layer 204a, the hardware I/O port 206b interoperates an adaptation layer identified as RFID right tag adaptation layer 204b, and the hardware I/O port 206c interoperates with an adaptation layer identified as RFID SBS adaptation layer 204c. The barcode adaptation layer 204a, the RFID right tag adaptation layer 204*b*, and the RFID SBS adaptation layer 204*c* interoperate with the healthcare application 202.

As described above with respect to FIG. 1, the adaptation layers 204*a*, 204*b* and 204*c* control the operation of the readers, barcode reader 208*a*, RT RFID reader 208*b*, and the SBS RFID reader 208*c* through the corresponding hardware I/O ports, 206*a*, 206*b*, 206*c*, respectively. The adaptation layers 204*a*, 204*b*, 204*c* receive event messages containing data received from the associated reader 208*a*, 208*b*, 208*c* and supply this information to the appropriate executable procedures in the healthcare application 202, which responds by retrieving the appropriate medical information and supplying it to a display screen (not shown) at the location of the associated reader.

A system which permits the addition of additional or new reader technologies, and/or readers of the same technology from different vendors, without requiring expensive and time consuming programming of corresponding adaptation layers for each such reader is desirable.

BRIEF SUMMARY OF THE INVENTION

In accordance with principles of the present invention, a medical information access and processing system includes a plurality of different wireless tag reader devices and a plurality of interfaces for receiving tag information, derived from reading a plurality of corresponding identification tags, from the tag reader devices. At least one repository of map information associates tag information received from the reader devices with reader device specific actions to be performed by a medical information access and processing system. A data processor uses the map information to associate tag information received from a specific reader device via an interface with a corresponding action to be performed by the medical information access and processing system and automatically initiates performance of the corresponding action by the medical information access and processing system.

DETAILED DESCRIPTION OF THE INVENTION

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor comprises any combination of, hardware, firmware, and/or software.

An executable application, as used herein, comprises code or machine readable instructions for conditioning the processor to implement predetermined functions, such as those of an operating system, a medical information access and processing system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

Figure 3:
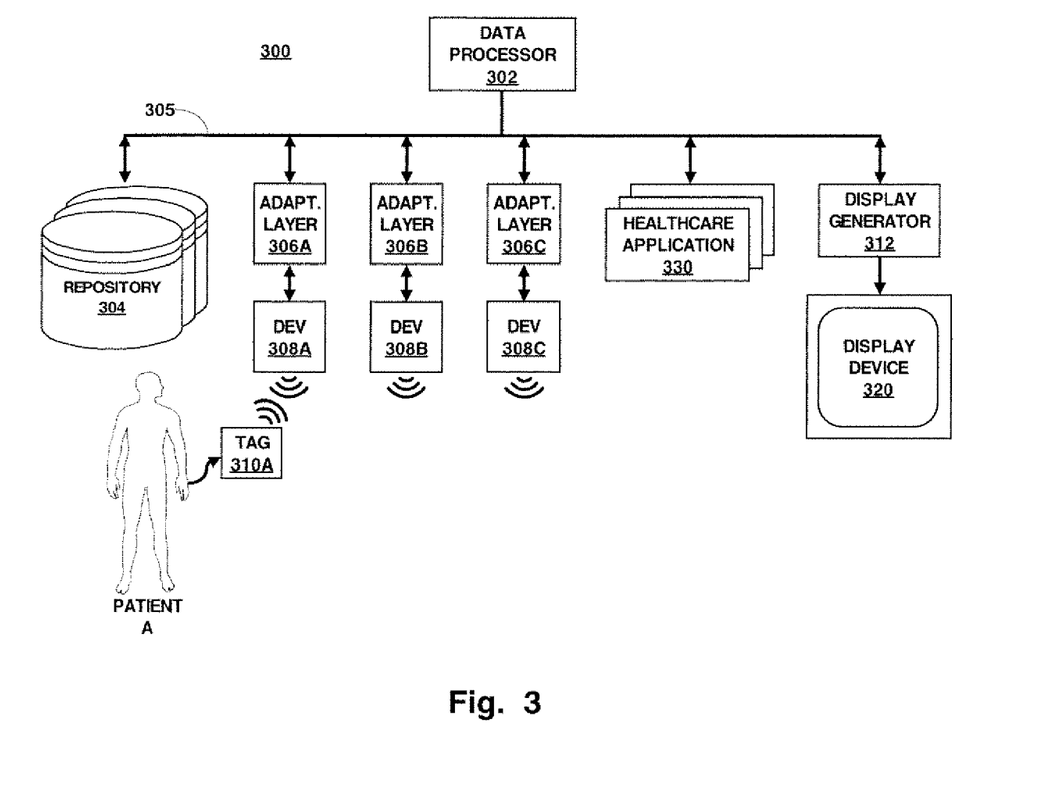
FIG. 3 is a block diagram illustrating a medical information access and processing system according to principles of the present invention.

FIG. 3 is a block diagram illustrating a medical information access and processing system 300 according to principles of the present invention. In FIG. 3, a plurality of different wireless tag reader devices, 308*a*, 308*b*, 308*c* are coupled to a corresponding plurality of adaptation layers 306*a*, 306*b*, 306*c*, respectively. The plurality of adaptation layers 306*a*, 306*b*, 306*c* are coupled to a data bus 305. At least one repository 304 of map information is also coupled to the data bus 305. Also coupled to the data bus 305 is a data processor 302, a memory device storing one or more executable applications 330 (which may be healthcare executable applications or non-healthcare executable applications), and a display generator 312. The display generator 312 is coupled to a display device 320.

In operation, the medical information access and processing system 300 operates under the control of the executable applications 330 as it is executed by the data processor 302. The plurality of adaptation layers 306*a*, 306*b*, 306*c*, operate as a plurality of interfaces for receiving tag information, derived from reading a plurality of corresponding identification tags, from the tag reader devices 308*a*, 308*b*, 308*c*. The at least one repository 304 of map information associates tag information received from the reader devices 308*a*, 308*b*, 308*c* with reader device specific actions to be performed by the medical information access and processing system 300. The data processor 302 uses the map information to associate tag information received from a specific reader device 308*a*, 308*b*, 308*c* via an adaptation layer 306*a*, 306*b*, 306*c* with a corresponding action to be performed by the medical information access and processing system 300 and automatically initiates performance of the corresponding action by the medical information access and processing system 300.

In FIG. 3, a patient A is wearing a wrist band containing a tag 310*a*. The tag includes a medium in which information relating to the particular patient, e.g. patient A, is encoded. More specifically, in the illustrated embodiment, the tag information includes data identifying the particular patient. When the tag 310*a* is brought within proximity of the tag reader device 308*a*, or the tag reader device 308*a* is brought within proximity of the tag 310*a*, the patient identification information in the tag is read by the tag reader device 308*a*. This information is supplied to the data processor 302 via the corresponding adaptation layer 306*a* and data bus 305. The plurality of adaptation layers 306*a*, 306*b*, 306*c* are implemented in the form of a plurality of different executable procedures for receiving and processing tag information from the plurality of different wireless tag reader devices 308*a*, 305*b*, 308*c*. Data stored in the repository 304 associates the patient identification information received from the tag reader device 308*a* with an action by the medical information access and processing system 300. In FIG. 3, the corresponding action to be performed by the medical information access and processing system 300 is to display an image on the display device 320 including medical information of the particular patient, e.g. patient A.

More specifically, in the illustrated embodiment, the data processor 302 operates as an internet browser server, providing data representing images in the form of web pages. The display generator 312 receives the image representative data from the data processor 302 and initiates display of the image within an Internet browser application window.

In a similar manner, tag data may be provided to a different tag reader, e.g. 308*b*, 308*c*, which may, for example, be located in a medical laboratory. When laboratory tests are performed for a particular patient, a bar code encoding patient identification information is affixed to the physical specimens from the particular patient. A barcode reader device 308*b*, 308*c* is used to scan the barcode on the specimen. The scanned data is supplied to the data processor 302 via the associated adaptation layer 306*b*, 306*c*. Data in the repository associates bar code data received from this bar code reader with an action to automatically open an internet window allowing a laboratory technician to enter laboratory test results in a patient medical record. There may be more than one barcode reader device 308*b*, 308*c* in the medical laboratory. In this case, this type of reader device, i.e. the reader devices in the medical laboratory, is associated with a particular laboratory result record section. In a different example, an admission desk may be provided with a single tag reader device. In this case that particular reader device is associated with opening an ADT internet page. That is, the at least one repository of map information 304 contains information which associates: (a) a particular type of reader device, and/or (b) one particular reader device, with received tag information received from a reader device.

Figure 4:
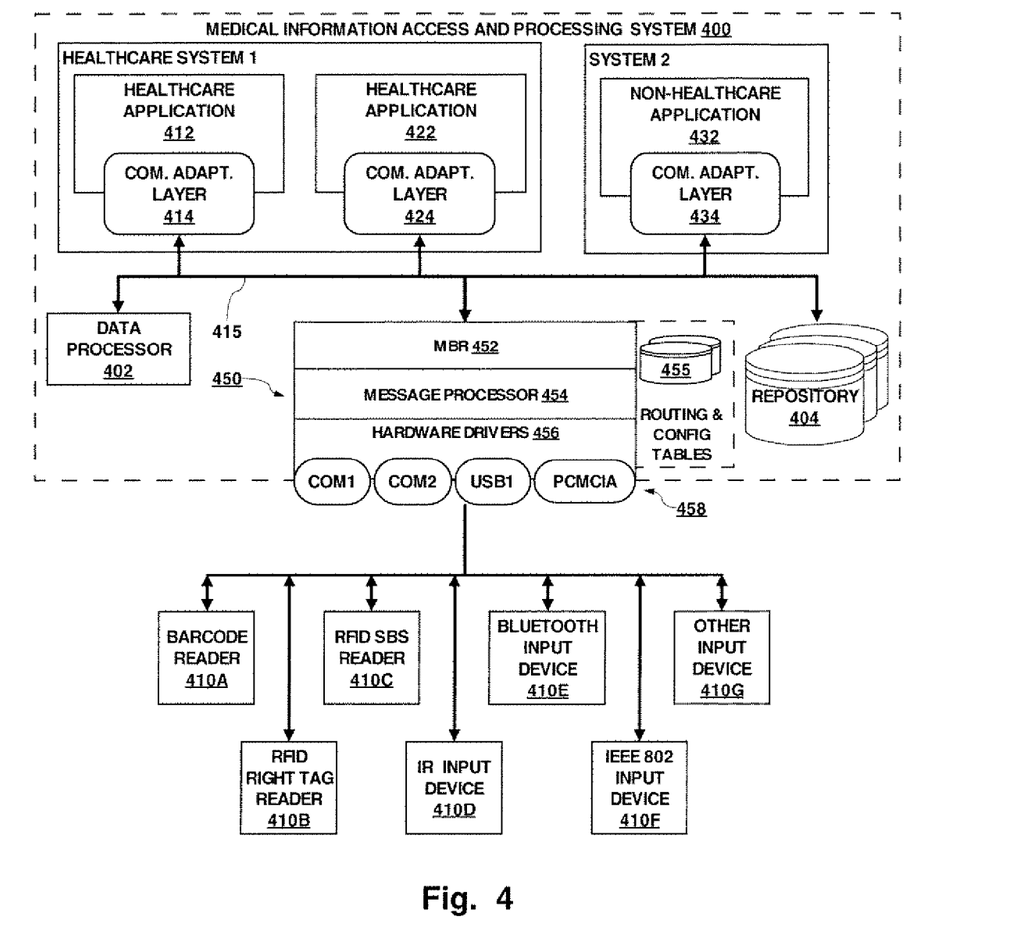
FIG. 4 and FIG. 5 are block diagrams of alternate embodiments of the medical information access and processing system illustrated in FIG. 3.

FIG. 4 is a block diagram of an alternate embodiment of the medical information access and processing system illustrated in FIG. 3. In FIG. 4, the medical information access and processing system 400 includes a plurality of different executable applications: e.g. healthcare system 1 including a first healthcare executable application 412 and a second healthcare executable application 422, and a non-healthcare system 2 including a non-healthcare executable application 432. A data processor 402 is coupled via a data bus 415 to a message based routing subsystem 450, at least one repository of map information 404, and a plurality of common adaptation layers 414, 424, and 434, respectively associated with the first healthcare executable application 412, the second healthcare executable application 422 and the non-healthcare executable application 432.

The message based routing subsystem 450 includes a message based router (MBR) 452, a message processor 454, and at least one repository of routing and configuration information 455. The message based routing subsystem 450 is coupled to a plurality of I/O ports 458 and further includes a plurality of hardware drivers 456 respectively corresponding to the hardware I/O ports 458. The I/O ports 458 are coupled to a plurality of different wireless tag reader devices including one or more of: (a) a bar code reader device 410*a*, (b) an RFID tag reader device 410*b*, 410*c*, (c) an infra-red (IR) technology reader device 410*d*, (d) a Bluetooth technology compatible device 410*e*, and (e) an IEEE 802 technology compatible device 410*f*. and (f) an input device 410*g* representing any other device capable of wirelessly reading tag data.

In general operation, the combination of the message based routing subsystem 450 and the plurality of common adaptation layers 414, 424, 434 form a plurality of interfaces for receiving tag information, derived from reading a plurality of corresponding identification tags, from the tag reader devices 410*a*, 410*b*, 410*c*, 410*d*, 410*e*, 410*f*, 410*g*. The message based routing subsystem 450 is implemented as an executable procedure executing under the control of the data processor 402.

The message based routing subsystem 450 generates messages having a standard format, and containing data representing at least: (a) the received tag data, (b) the identity of the specific tag reader device generating the tag data, (c) the system (e.g. healthcare system 1, non-healthcare system 2) to which the message is to be delivered, and (d) the executable application 412, 422, 432 to which the message is to be delivered. Other data may be included in the message, including the type of tag reader device 410*a*, 410*b*, 410*c*, 410*d*, 410*e*, 410*f*, 410*g* from which tag data was received, the length of the message, error detection and/or correction codes, other contextual data, and so forth.

The common adaptation layers 414, 424, 434 are also implemented as executable procedures executing under control of the data processor 402. The common adaptation layers 414, 424, 434 are programmed to receive messages in the standard format, to extract data from messages intended to be delivered to the executable application 412, 422, 432 associated with that common adaptation layer, 414, 424, 434, respectively, and to provide the extracted data to the associated executable application 412, 422, 432. In this manner, any differences between tag reader devices 410*a*, 410*b*, 410*c*, 410*d*, 410*e*, 410*f*, 410*g* are handled within the message based routing subsystem 450, and standard formatted messages are passed on to the plurality of executable applications 412, 422, 432.

Because messages having a standard format are supplied to the common adaptation layers 414, 424, 434, a single adaptation layer module needs to be programmed for and coupled to the respective executable applications 412, 422, 432, regardless of the number of tag reader devices 410*a*, 410*b*, 410*c*, 410*d*, 410*e*, 410*f*, 410*g*, the number of different technologies used by the tag reader devices 410*a*, 410*b*, 410*c*, 410*d*, 410*e*, 410*f*, 410*g*, and/or the number of different vendors which manufacture the tag reader devices 410*a*, 410*b*, 410*c*, 410*d*, 410*e*, 410*f*, 410*g*. This permits easy expansion for new tag reader devices 410*a*, 410*b*, 410*c*, 410*d*, 410*e*, 410*f*, 410*g*, new technologies and/or new vendors because the message based routing subsystem 450 is readily modified to accommodate the new devices, and the message based routing subsystem 450 is not closely coupled to the executable applications 412, 422, 432. Thus, in FIG. 4, the plurality of different wireless tag reader devices 410*a*, 410*b*, 410*c*, 410*d*, 410*e*, 410*f*, 410*g* may include different types of wireless tag reader devices including two or more of: (a) a bar code reader device 410*a*, (b) an RFID tag reader device 410*b*, 410*c*, (c) an infra-red technology reader device 410*d*, (d) a Bluetooth technology compatible device 410*e*, (e) an IEEE 802 technology compatible device 410*f*, and/or (f) other tag reader device 410*g* capable of wirelessly reading tag data from a medium.

The message based routing subsystem 450, including the message based router 452, the message processor 454 and the hardware drivers 456, is implemented as one or more executable procedures executing on the data processor 402. The hardware drivers 456 are capable of controlling and receiving tag information from the plurality of tag reader devices 410*a*, 410*b*, 410*c*, 410*d*, 410*e*, 410*f*, 410*g*. The data received from the hardware drivers 456 is passed to the message processor 454. The message processor 454 accesses the communication information in the routing and configuration tables 455. The communication information in the routing and configuration tables 455 associates communication data supporting message communication from a tag reader device interface (e.g. the message based routing subsystem 450) receiving tag information from a specific reader device 410*a*, 410*b*, 410*c*, 410*d*, 410*e*, 410*f*, 410*g* with a particular application 412, 422, 432 of the plurality of different executable applications. In the illustrated embodiment, the communication information in the routing and configuration tables 455 includes: (a) routing data enabling message routing, and/or (b) configuration data enabling generation of a message having the standard format, for supporting the message communication.

More specifically, in the illustrated embodiment, the routing and configuration tables 455 include data which associates the respective tag reader devices 410a, 410b, 410c, 410d, 410e, 410f, 410g with a corresponding system, e.g. healthcare system 1 or non-healthcare system 2, and a particular executable application, 412, 422, 432. The message processor 454 uses the configuration data to generate a message containing the tag data, the identity of the specific tag reader device 410a, 410b, 410c, 410d, 410e, 410f, 410g which provided the tag data, and the identities of the system, e.g. healthcare system 1 or non-healthcare system 2, and a particular executable application, 412, 422, 432 to which the message is to be delivered in the standard format. The message based router 452 provides that message to the common adaptation layers 414, 424, 434 via the data bus 415 under the control of the data processor 402. As described above, the data processor 402 accesses the at least one repository 404 to associate the tag information received from the specific reader device 410a, 410b, 410c, 410d, 410e, 410f, 410g with a corresponding action to be performed by the medical information access and processing system 400 and for automatically initiating performance of that corresponding action by the medical information access and processing system 400.

More specifically, the at least one repository of map information 404 contains data associating tag information received from a specific reader device 410a, 410b, 410c, 410d, 410e, 410f, 410g with a reader device specific action to be performed by a particular application of the plurality of different executable applications 412, 422, 432. The data processor 402 uses the map information from the at least one repository 404 to associate tag information received from a specific reader device 410a, 410b, 410c, 410d, 410e, 410f, 410g with a corresponding action to be performed by a particular application of the plurality of different executable applications 412, 422, 432 and for automatically initiating performance of that corresponding action by the particular application. In this manner, the at least one repository of map information 404, the routing and configuration information 455 and the data processor 402 form an adaptation layer for adaptively automatically initiating performance of a corresponding action by a particular executable application 412, 422, 432 in response to tag information received from a specific reader device 410a, 410b, 410c, 410d, 410e, 410f, 410g.

Figure 5:
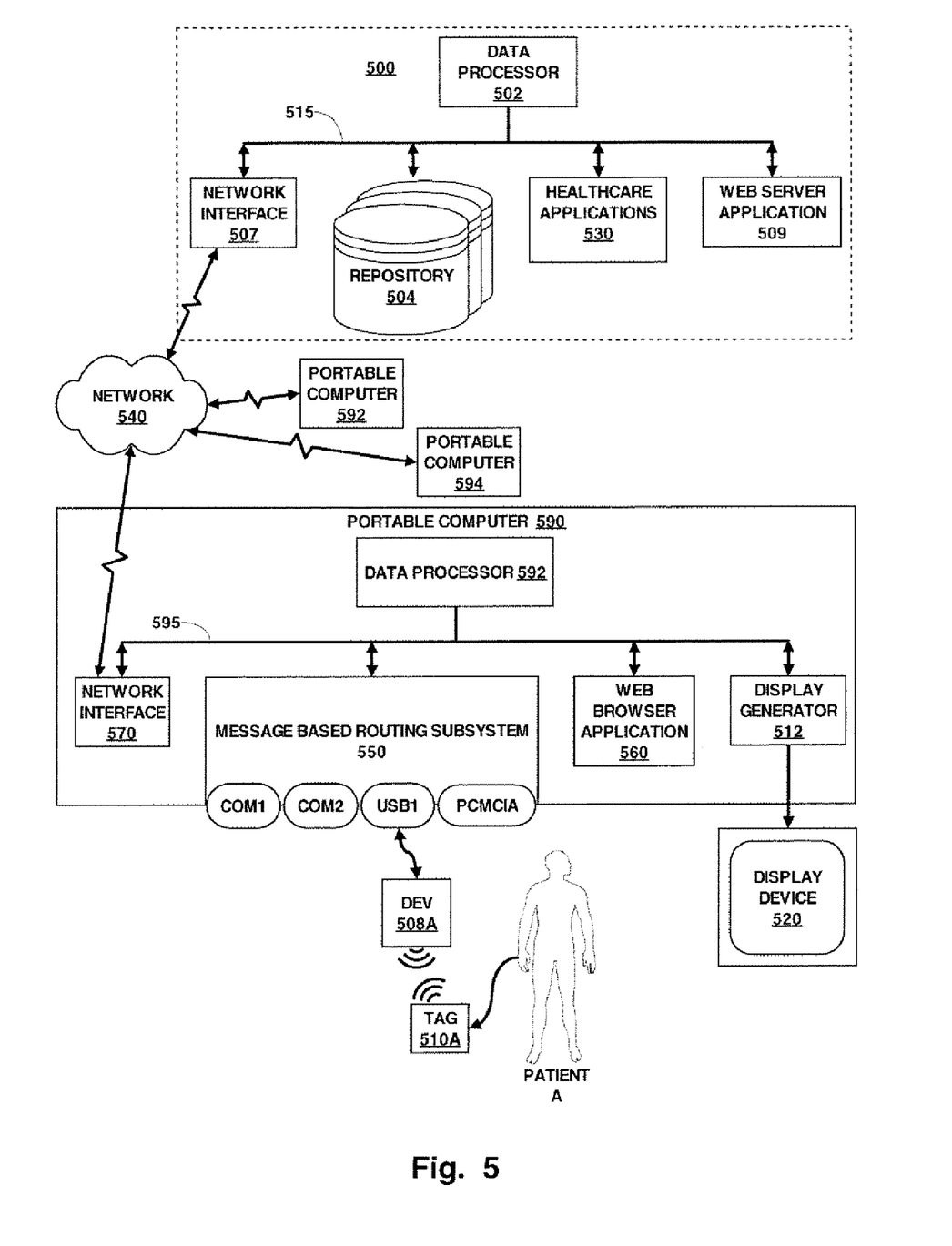

FIG. 5 is a block diagram of another alternate embodiment of the medical information access and processing system illustrated in FIG. 3. In FIG. 5, a medical information access and processing system 500 includes a data processor 502, at least one repository of map data 504, a plurality of executable applications 530, a network interface 507, and a web server executable application 509, coupled together via a data bus 515. The network interface 515 is coupled to a network 540. The network 540 may include wired and/or wireless links between network nodes and may include a local area network (LAN) and/or a wide area network such as the internet.

The network 540 is also coupled to a plurality of portable computers 590, 592, 594. The portable computer 590 is illustrated in more detail in FIG. 5, and is representative of the portable computers 592 and 594. In the portable computer 590, a data processor 592 is coupled to a message based routing subsystem 560, a web browser application 550, a display generator 512 and a network interface 570. The display generator 512 is coupled to a display device 520. The message based routing subsystem 550 is coupled to a tag reader device 508a.

In operation, tag information, e.g. generated by the tag reader device 508a from reading a tag 510a, is provided to the USB port of the portable computer 590. As described above with respect to the message based routing subsystem 450 in FIG. 4, the message based routing subsystem 550 forms a message in a standard format containing the received tag information, along with data identifying the particular tag reading device 510a which generated the tag information, and the particular executable application of the plurality of executable applications 530 in the medical information access and processing system 500 to which the message is to be delivered, and other data. This data is supplied to the data processor 502 in the medical information access and processing system 500 via the network interface 570 in the portable computer, the network 540 and the network interface 507 in the medical information access and processing system 500. The data processor 502 in the medical information access and processing system 500 accesses map information in the at least one repository 504 to determine the action to be performed by the particular executable application of the plurality of executable applications 530 in response to the receipt of tag data from the particular tag reader device 508a, and conditions the particular executable application to perform that action.

The message generated by the message based routing subsystem 550 may be supplied to the medical information access and processing system 500 by the web browser application 560 in the form of a URL with an associated query string and/or arguments. The submitted URL may be processed by the web server application 509 in the medical information access and processing system 500. The web server application 509 provides the message to the data processor 502 which accesses the map information from the repository 504, and conditions the appropriate executable application 530 to perform the desired action. The results of the action performed by the medical information access and processing system 500 may be supplied to the portable computer 590 via the web server application 509 in the medical information access and processing system 500 and received and processed by the web browser application 560 in the portable computer 590.

For example, the portable computer 590 may be used by a doctor making rounds in a ward. The doctor enters a patient room, and moves the tag reader device 508a into the proximity of the tag 510 on the wrist band of the patient A. The tag 510 contains data representing identification information of the patient A. The desired action associated with the tag reader device 508a attached to the portable computer 590 (as contained in the map information in the repository 504) is to access and display patient medical data (e.g. vital signs, pharmacy laboratory results, etc.) for the patient A whose wrist band tag was scanned.

The tag information from the tag 510a is provided to the medical information access and processing system 500 as described above. The appropriate one of the plurality of executable applications 530 in the medical information access and processing system 500 performs the desired action, i.e. retrieves the medical data for patient A, and supplies the results to the web server application 509. Data representing a web page image containing the desired medical data is generated by the web server application 509 and supplied to the web browser application 560 in the portable computer 590 via the network 540. The web browser application 560 conditions the display generator 512 to generate a signal representing the web page image of the medical data and to provide that signal to the display device 520, which displays the image. The doctor can view this image on the display device 520. Data entry is also possible if the web page image also includes form fields.

In this example, the doctor was able to access and view medical records of the patient A without manually entering the patient identification information, a process which is repetitive, time consuming and potentially unreliable. A system as described above and illustrated in the figures permits multiple tag reader devices to provide data to different executable applications in a medical information access and processing system. The number, type and vendor of such devices may also be expanded without requiring a major reprogramming of the executable applications. By associating specific actions to be performed by executable applications in the medical information access and processing systems with corresponding specific tag reader devices and/or tag reader device types, clinician time may be saved and accuracy improved.

Glossary of Terms, Abbreviations and Acronyms

Workflow Context (WC) This refers to a particular point-of-care situation in a Clinical workflow process. E.g. in order to edit a patients address, the user should first navigate to the address specific screen and then update the address information. The address specific screen identifies the workflow context within which a user be to update patient address. Each context is usually mapped to one or more unique identifier/s, such as patient ID and/or user ID and/or address specific ID, etc in the Clinical workflow process.

Context Information conveyed from a first executable application to a second executable application facilitating automatic data access by the second executable application and including, for example, patient identifier, patient specific information, MRN and information required by the second executable application in executing a command made by a user while concurrently operating the first executable application. The context information may be conveyed in the data fields of a URL, for example.

RFID Radio Frequency Identification

Healthcare IT Healthcare Information Technology

Healthcare IT System Consists of one or more healthcare applications including hardware, software components within an enterprise.

Enterprise Healthcare IT System Consists of one or more Healthcare IT systems.

Alpha-search A criterion by which an element of information is sought using a specific name or pattern. A matching item or list of items may be found as a result of an alpha search MRN Medical Record Number. A unique identifier associated with a patient.

What is claimed is:

1. A medical information access and processing system, comprising:
   a plurality of different wireless tag reader devices;
   a plurality of interfaces for receiving tag information, derived from reading a plurality of corresponding identification tags, from said tag reader devices;
   at least one repository of map information for associating tag information received from reader devices with reader device specific actions to be performed by a medical information access and processing system; and
   a data processor for using said map information to associate tag information received from a specific reader device via an interface with a corresponding action to be performed by a medical information access and processing system and for automatically initiating performance of said corresponding action by said medical information access and processing system, said at least one repository of map information and said data processor comprise an adaptation layer for adaptively automatically initiating performance of a corresponding action by a particular application in response to tag information received from a specific reader device.

2. A system according to claim 1, wherein:
   said tag information includes data identifying a particular patient; and
   said corresponding action by said medical information access and processing system comprises display of an image including medical information of said particular patient.

3. A system according to claim 2, including a display generator for initiating display of said image within an Internet browser application window.

4. A system according to claim 1, wherein said at least one repository of map information contains information which associates at least one of:
   (a) a particular type of reader device, and (b) one particular reader device, with received tag information received from a reader device.

5. A system according to claim 1, wherein said plurality of interfaces comprise a plurality of different executable procedures for receiving and processing tag information from said plurality of different wireless tag reader devices.

6. A system according to claim 1, wherein said medical information access and processing system further comprises:
   a plurality of different executable applications; and
   at least one repository of communication information for associating communication data supporting message communication from an interface receiving tag information from a specific reader device with a particular application of said plurality of different executable applications.

7. A system according to claim 6, wherein said communication information comprises at least one of: (a) routing data enabling message routing, and (b) configuration data enabling generation of a message format, for supporting said message communication.

8. A system according to claim 1, wherein:
   said medical information access and processing system comprises a plurality of different executable applications;
   said at least one repository of map information contains data associating tag information received from a specific reader device with a reader device specific action to be performed by a particular application of said plurality of different executable applications; and
   said data processor uses said map information to associate tag information received from a specific reader device with a corresponding action to be performed by a particular application of said plurality of different executable applications and for automatically initiating performance of said corresponding action by said particular application.

9. A system according to claim 8 wherein said plurality of interfaces comprise:
   a subsystem for receiving tag information, derived from reading said plurality of corresponding identification tags, from said tag reader devices, and generating messages having a standard format, and containing data representing at least: (a) said received tag data, and (b)

the identity of a specific tag reader device generating said tag data, and (c) a particular one of the plurality of executable applications to which a message is to be delivered; and a plurality of common adaptation layers, respectively associated with said plurality of executable applications, for receiving messages from said tag information receiving subsystem, extracting data from messages intended to be delivered to the associated executable application, and providing the extracted data to the associated executable application.

10. A system according to claim 9 wherein the tag information receiving subsystem comprises:

hardware drivers, coupled to said plurality of wireless tag reader devices, capable of controlling said plurality tag reader devices and receiving tag information from said plurality of tag reader devices;

at least one repository of communication information supporting message communication from a specific tag reader device to a particular executable application of said plurality of executable applications;

a message processor, coupled to said hardware drivers and said at least one repository of communication information, for accessing the communication information in said at least one repository and generating a message containing said tag data, said identify of said specific tag reader device and said particular executable application to which the message is to be delivered; and a message based router, to provide said message to said plurality of common adaptation layers.

11. A system according to claim 10 wherein:

said at least one repository of communication information further contains configuration data enabling generation of a message having said standard format; and said message processor accesses said configuration data for forming a message having said standard format.

12. A system according to claim 10 wherein:

said at least one repository of communication information further contains routing data; and said message processor accesses said message routing data enabling message routing to said particular executable application.

13. A system according to claim 1, wherein said plurality of different wireless tag reader devices comprise one or more of: (a) a bar code reader device, (b) an REID tag reader device, (c) an infra-red technology reader device, (d) a Bluetooth technology compatible device, and (e) an IEEE 802 technology compatible device.

14. A system according to claim 1, wherein said plurality of different wireless tag reader devices comprise different types of wireless tag reader devices including two or more of: (a) a bar code reader device, (b) an RFID tag reader device, (c) an infra-red technology reader device, (d) a Bluetooth technology compatible device, and (e) an IEEE 802 technology compatible device.

15. A medical information access and processing system, comprising:

a plurality of different wireless tag reader devices;

a plurality of interfaces for receiving tag information, derived from reading a plurality of corresponding identification tags, from said tag reader devices;

at least one repository of map information for associating received tag information received from reader devices with reader device specific actions to be performed by a medical information access and processing system;

a data processor for using said map information to associate tag information received from a specific reader device via an interface with a corresponding action to be performed by an application of a plurality of executable applications and for automatically initiating performance of said corresponding action by said application;

a subsystem for receiving tag information, derived from reading said plurality of corresponding identification tags, from said tag reader devices, and generating messages having a standard format, and containing data representing at least: (a) said received tag data, and (b) the identity of a specific tag reader device generating said tag data, and (c) a particular one of the plurality of executable applications to which a message is to be delivered: and a plurality of common adaptation layers, respectively associated with said plurality of executable applications, for receiving messages from said tag information receiving subsystem, extracting data from messages intended to be delivered to the associated executable application, and providing the extracted data to the associated executable application.

16. A system according to claim 15, wherein:

said at least one repository of map information associates received tag information received from a specific reader device with a reader device specific action to be performed by a particular application of said plurality of different executable applications; and said data processor uses said map information to associate tag information received from a specific reader device with a corresponding action to be performed by a particular application of said plurality of different executable applications and for automatically initiating performance of said corresponding action by said particular application.

17. A system according to claim 15 further comprising:

at least one portable computer, comprising:

at least one wireless tag reader device;

at least one tag information receiving subsystem for receiving tag information, derived from reading said plurality of corresponding identification tags, from said at least one tag reader device, and generating messages having a standard format, and containing data representing at least: (a) said received tag data, and (b) the identity of a specific tag reader device generating said tag data, and (c) a particular one of the plurality of executable applications to which a message is to be delivered; and a network interface, coupled to a communication network, for providing said message to said network; and a network interface, coupled to a communication network, for receiving said messages and providing them to said plurality of common adaptation layers, respectively associated with said plurality of executable applications, for receiving messages from said tag information receiving subsystem, extracting data from messages intended to be delivered to the associated executable application, and providing the extracted data to the associated executable application.

18. A system according to claim 15 wherein the tag information receiving subsystem comprises:

hardware drivers, coupled to said plurality of wireless tag reader devices, capable of controlling said plurality tag reader devices and receiving tag information from said plurality of tag reader devices;

at least one repository of communication information supporting message communication from a specific tag reader device to a particular executable application of said plurality of executable applications;

a message processor, coupled to said hardware drivers and said at least one repository of communication information, for accessing the communication information in said at least one repository and generating a message containing said tag data, said identify of said specific tag reader device and said particular executable application to which the message is to be delivered; and a message based router, to provide said message to said plurality of common adaptation layers.

19. A system according to claim 18 wherein:

said at least one repository of communication information further contains configuration data enabling generation of a message having said standard format; and said message processor accesses said configuration data for forming a message having said standard format.

20. A system according to claim 18 wherein:

said at least one repository of communication information further contains routing data; and said message processor accesses said message routing data enabling message routing to said particular executable application.

* * * * *